United States Patent [19]

VandenBerg

[11] Patent Number: 4,827,061
[45] Date of Patent: May 2, 1989

[54] CHRYSANTHEMUM PLANT NAMED CARICIA

[75] Inventor: Cornelis P. VandenBerg, Salinas, Calif.

[73] Assignee: Yoder Brothers, Inc., Barberton, Ohio

[21] Appl. No.: 229,116

[22] Filed: Aug. 5, 1988

Related U.S. Application Data

[62] Division of Ser. No. 187,654, Apr. 28, 1988.

[51] Int. Cl.⁴ .............................................. A01H 5/00
[52] U.S. Cl. ....................................................... 800/1
[58] Field of Search ............................. 800/1; Plt./74

Primary Examiner—Robert E. Bagwill
Attorney, Agent, or Firm—Foley & Lardner, Schwartz, Jeffery, Schwaab, Mack, Blumenthal & Evans

[57] ABSTRACT

A Chrysanthemum plant named Caricia particularly characterized by its flat capitulum form; anemone capitulum type; very soft pink ray floret color; diameter across face of capitulum of up to 7 cm at maturity, with diameter of anemone cushion up to 22 mm; uniform eight week photoperiodic flowering response to short days; peduncle length ranging from 8 to 18 cm on open, terminal sprays; medium plant height when grown as a single stem spray cut mum; and excellent tolerance to low temperatures for bud initiation and flower development.

2 Claims, 3 Drawing Sheets

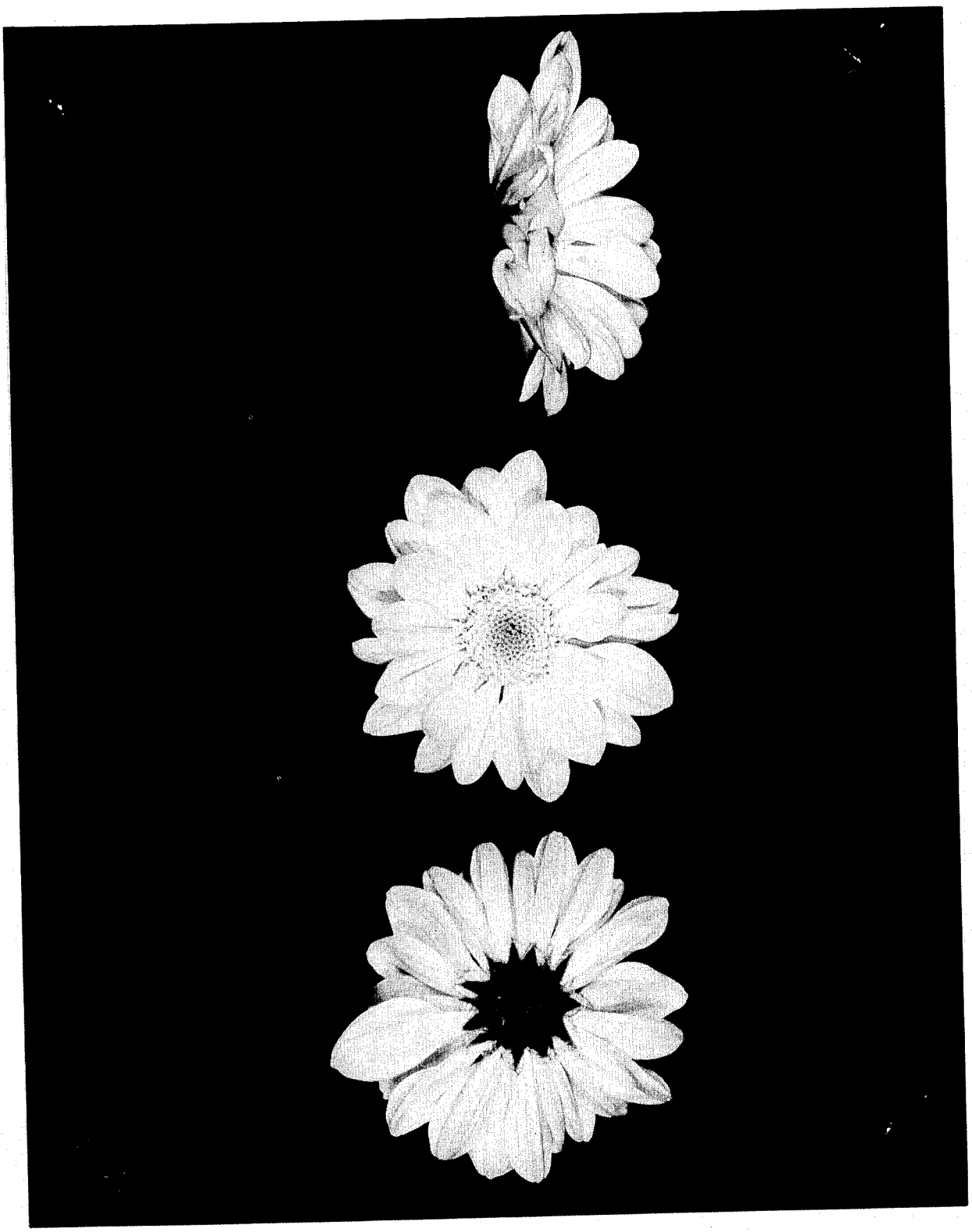

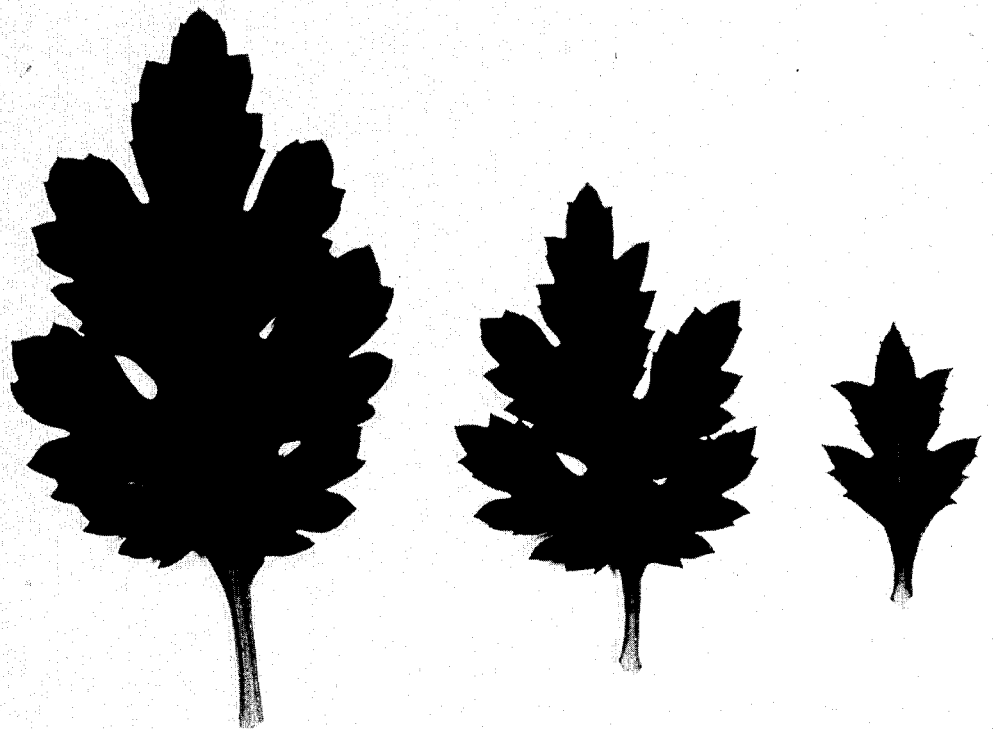
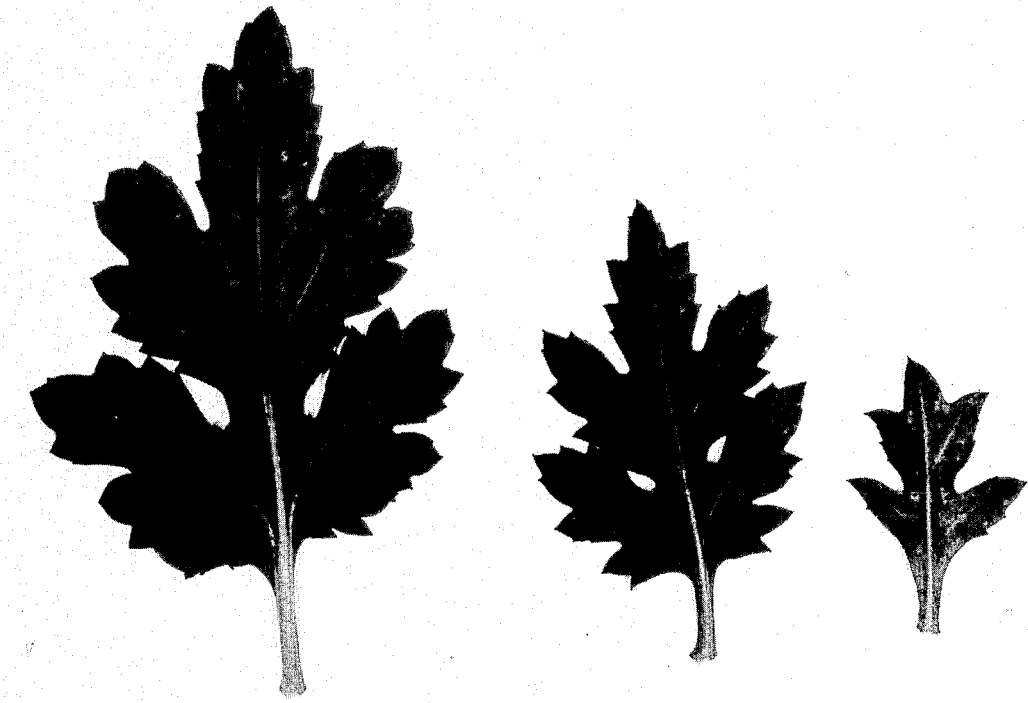

CHRYSANTHEMUM PLANT NAMED CARICIA

This is a division of application Ser. No. 187,654, filed Apr. 28, 1988.

The present invention comprises a new and distinct cultivar of Chrysanthemum, botanically known as *Dendranthema grandiflora*, and referred to by the cultivar name Caricia.

Caricia, identified as 84567001, was originated from a cross made by Cornelis P. VandenBerg in a controlled breeding program in Salinas, Calif. in 1984.

The female parent and the male parent in Caricia were both unnamed seedlings, identified respectively as 79I70026 and 78@24002.

Caricia was discovered and selected as one flowering plant within the progeny of the stated cross by Cornelis P. VandenBerg in May 1985 in a controlled environment in Salinas, Calif.

The first act of asexual reproduction of Caricia was accomplished when vegetative cuttings were taken from the initial selection in July 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Caricia are firmly fixed and are retained through successive generations of asexual reproduction.

Caricia has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Caricia, which, in combination, distinguish this Chrysanthemum as a new and distinct cultivar:

1. Flat capitulum form.
2. Anemone capitulum type.
3. Very soft pink ray floret color.
4. Diameter across face of capitulum up to 7 cm at maturity, with diameter of anemone cushion up to 22 mm.
5. Uniform eight week photoperiodic flowering response to short days.
6. Peduncle length ranging from 8 to 18 cm on open terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Caricia.

FIG. 1 is a black and white photograph of Caricia grown as a single stem cut spray mum.

FIG. 2 is a black and white photograph of three views of the inflorescence of Caricia.

FIG. 3 is a black and white photograph showing the upper and under sides of the leaves of Caricia at three stages of development (mature, intermediate and immature).

The combination of very soft pink ray floret color and flat anemone capitulum form and type is not represented in any of the commercial cultivars known to the inventor. The cultivar most similar in comparison to Caricia is the inventor's new cultivar Fina. Reference is made to Chart A, which compares certain characteristics of Caricia to the same characteristics of Fina.

Similar traits are capitulum form and type, plant height, flowering response period, and low temperature tolerance. The ray floret color of Caricia is a very soft pink, whereas Fina is clear white. Also, Caricia has a significantly smaller diameter of capitulum than Fina.

In the following description, color references are made to The Royal Horticultural Society Colour Chart. The color values were determined on plant material grown in Salinas, Calif. on Jan. 29, 1988.

Classification:
  Botanical.—*Dendranthema grandiflora*, cv. Caricia.
  Commercial.—Anemone cut spray mum.

INFLORESCENCE

A. Capitulum:
  Form.—Flat.
  Type.—Anemone.
  Diameter across face.—Up to 7 cm at maturity.
  Diameter of anemone cushion.—Up to 22 mm.
B. Corolla of ray florets:
  Color (general tonality from a distance of three meters).—Very soft pink.
  Color (upper surface).—56D, fading to almost white with 56D overcast.
  Color (under surface).—56D.
  Shape.—Flat; oblong.
C. Corolla of disc florets:
  Color (mature).—155C, with tips of anemone disc florets 6A to 6B.
  Color (immature).—Closest to 144B to 145A.
D. Reproductive organs:
  Androecium.—Present on disc florets only; scant pollen.
  Gynoecium.—Present on both ray and disc florets.

PLANT

A. General appearance:
  Height.—Medium; 90 to 100 cm as a single stem cut mum with two long day weeks prior to short days.
B. Foliage:
  Color (upper surface).—147A.
  Color (under surface).—147B.
  Shape.—Lobed and slightly serrated.

The cultivar Caricia is commercially available from Yoder Brothers, Inc., P.O. Box 230, Barberton, Ohio 44203, and its authorized distributors.

CHART A

| COMPARISON OF CARICIA AND FINA | | |
|---|---|---|
| | Caricia | Fina |
| Ray floret color | Very soft pink | White |
| Capitulum form and type | Flat Anemone | Flat Anemone |
| Spray formation | Terminal | Terminal |

CHART A-continued
COMPARISON OF CARICIA AND FINA

|  | Caricia | Fina |
|---|---|---|
|  | 8 to 18 cm peduncles | 8 to 20 cm peduncles |
| Diameter across face of capitulum | Up to 7 cm | Up to 10 cm |
| Plant height | Medium | Medium |
| Flowering response period | 8 weeks | 8 weeks |
| Low temperature tolerance | Excellent | Excellent |

COMPARISONS MADE OF PLANTS GROWN AS SINGLE STEM SPRAY CUT MUMS IN SALINAS, CALIFORNIA

I claim:
1. Cut flowers of the Chrysanthemum plant named Caricia.
2. Propagating material of the Chrysanthemum plant named Caricia.

* * * * *